United States Patent [19]
Adamski et al.

[11] Patent Number: 5,220,168
[45] Date of Patent: Jun. 15, 1993

[54] METHOD AND APPARATUS FOR DETERMINING MOISTURE CONTENT OF MATERIALS

[75] Inventors: Joseph R. Adamski, Sudbury; J. Scott Petty, Hanover; William E. Nothe, Billerica, all of Mass.

[73] Assignee: Raytheon Company, Lexington, Mass.

[21] Appl. No.: 869,998

[22] Filed: Apr. 16, 1992

[51] Int. Cl.$^5$ .............................................. G01N 21/35
[52] U.S. Cl. .................................... 250/339; 250/341; 250/353
[58] Field of Search .................. 250/339, 341, 353

[56] References Cited

U.S. PATENT DOCUMENTS

| | | | |
|---|---|---|---|
| 4,286,327 | 8/1981 | Rosenthal et al. | 250/339 |
| 4,755,678 | 7/1988 | Izatt et al. | 250/339 |
| 4,857,735 | 8/1989 | Noller | 250/339 |
| 5,017,787 | 5/1991 | Sato et al. | 250/339 |

Primary Examiner—Carolyn E. Fields
Attorney, Agent, or Firm—William R. Clark; Richard M. Sharkansky

[57] ABSTRACT

Method and apparatus for determining moisture content of materials by irradiating a sample of unknown moisture content with a narrow frequency band of light at a first wavelength during a first time period and a narrow frequency band of light of a second wavelength during a second time period. The two wavelengths of light have different water absorptive characteristics, and therefore are reflected by varying degrees depending on the surface moisture on the material. The respective reflections are measured by a single common detector, and a value corresponding to the ambient light is subtracted from each measurement. A ratio of the resultant values is then correlated with data derived from precalibration measurements of samples of known moisture content.

18 Claims, 4 Drawing Sheets

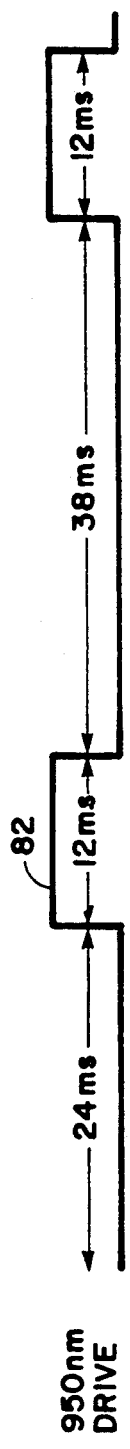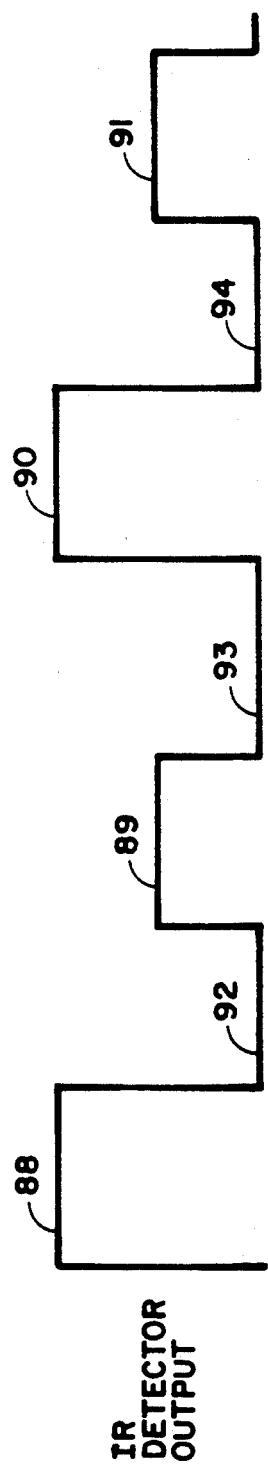

METHOD AND APPARATUS FOR DETERMINING MOISTURE CONTENT OF MATERIALS

BACKGROUND OF THE INVENTION

This invention generally relates to method and apparatus for determining the moisture content of materials, and more particularly relates to a dual wavelength infrared technique for measuring moisture content.

As is well known, knowledge about the exact amount of water or moisture present in materials or substances is important for the accurate control of many industrial processes. For example, in the process of making asphalt paving material, sand and gravel, which are collectively referred to as aggregate, are generally mixed with a bituminous or asphalt liquid. However, if the aggregate is not sufficiently hot, the asphalt liquid will not properly adhere to the sand and gravel. Therefore, a large burner is typically used to heat the aggregate before mixing the aggregate with the asphalt liquid. In such process, it is important to know the initial moisture content of the aggregate because that effects how many BTUs are required to heat the aggregate to a sufficient temperature. Therefore, with knowledge regarding the moisture content of the aggregate, the burner can be continuously and accurately regulated. If too little heat is applied, the aggregate will not be sufficiently heated; conversely, if too much heat is applied, the aggregate may be too hot and the energy efficiency of the process will be degraded. In this and other industrial processing systems, the various stages such as the regulation of the burner are controlled by a process computer. In such arrangement, it is desirable to provide the process computer continuously with real time electrical signals representative of the moisture content of the aggregate so that the burner firing rate can be optimized.

Moisture content is generally defined as the ratio of water weight divided by the material weight plus the water weight. One conventional prior art method for determining moisture content is referred to as the water evaporation method. A sample of a material such as aggregate is first weighed, and then it is heated for a sufficient period of time to evaporate or drive off all of the moisture within the sample. Next, the sample is reweighed. The material weight plus water weight is, of course, provided by the initial weighing, and the water weight is the difference between the first weighing and the reweighing after the water has been driven off. One problem with this method is that it requires a substantial amount of time and is labor intensive. Further, the method is not readily adapted to a continuous monitoring system that determines the real time moisture content of a substance such as aggregate immediately prior to a stage where knowledge of moisture content is critical. In fact, aggregate would typically not have a homogenous moisture content, and by the time that one sample on a conveyor belt is analyzed, the aggregate entering the next stage may have an entirely different moisture content.

Another method for determining the moisture content of materials or substances such as aggregate is referred to as the microwave method. Microwave energy is propagated through the aggregate and its conveyor belt, and the theory is that the magnitude of the microwave energy on the other side of the conveyor is a function of the water or moisture content in the aggregate. That is, the more moisture that is present in the aggregate, the more attenuated the microwave energy will be at a detector on the opposite side. This method has a number of apparent disadvantages. First, a relatively high microwave energy power level is required to compensate for energy losses in the conveyor belt and the aggregate itself. Second, the accuracy of the measurement is very limited. That is, it is very difficult to measure small incremental changes in power level caused by absorption by the moisture. Further, the consistency, lossiness and thickness of the aggregate must be very accurately regulated to prevent these factors from becoming variables in the microwave measurements.

Another method of determining moisture content of a sample takes advantage of the fact that infrared energy is known to be absorbed by water at very specific wavelengths. That is, the absorptivity of infrared energy by water or moisture is known to be dependent on wavelength. In one commercially available system, the material, such as aggregate moving on a conveyor belt, is illuminated with broadband infrared energy, and a reflection sensor is positioned immediately above the aggregate. The reflected infrared energy power spectrum is altered according to the amount of moisture on the surface of the aggregate. For example, if the sample has a relatively large amount of moisture on the surface, reflection of energy at wavelengths of high water absorption will be greatly reduced while reflections of energy at wavelengths of low water absorption will be less attenuated by the surface moisture. The spectrum of reflected energy is filtered using wavelength selective optics mounted in a chopper wheel. More particularly, the sensor includes a stationary broadband infrared detector positioned behind a chopper wheel having a plurality of narrow band pass filters each disposed at a different angular orientation around the wheel. Thus, as the wheel rotates, narrow band pass filters of different wavelengths sequentially cover the infrared detector. During a first time period, the infrared detector is exposed to infrared energy of a first wavelength $\lambda 1$ having a first water absorption characteristic because this is the only light permitted to pass the filter disposed in front of the infrared detector. Then, during a second time period, the infrared detector is exposed to infrared energy of a second wavelength $\lambda 2$ having a second water absorption characteristic because this is the only light permitted to pass the filter disposed in front of the infrared detector during the second time period. As a result, the detector provides sequential pulses having amplitudes which are a function of the absorption of infrared energy of the respective wavelengths by the surface moisture of the material. For example, the reflection of infrared energy at one of the wavelengths $\lambda 1$ is not readily absorbed by the surface moisture and thus provides a reference value relating to the surface parameters or characteristics of the material (e.g. how much side reflection there is). The reflection of infrared energy at the other wavelength $\lambda 2$ is more readily absorbed in surface moisture and thus provides a measure of the surface moisture. By taking the ratio of the pulses for $\lambda 1$ and $\lambda 2$, a value proportional to the surface moisture is obtained, and surface moisture generally corresponds to the moisture content of the material. The ratio of $\lambda 1$ and $\lambda 2$ can be compared or correlated with data derived from similar measurements previously taken on materials or substances of known moisture content.

The chopper wheel approach, however, has some drawbacks. First, the chopper wheel has to be rotated thereby requiring a drive motor and other associated moving mechanical components that increase the cost and reduce the reliability of the sensor. Also, the transmitted power levels of energy at λ1 and λ2 are relatively weak because they are only a portion of the broadband energy used to illuminate the sample. As such, the ambient light becomes a much more critical factor thus sometimes necessitating the use of shields to shade the sensor and sampled region. It is also apparent that the sensor would have a relatively low signal-to-noise ratio.

SUMMARY OF THE INVENTION

In accordance with the invention, a method comprises the steps of irradiating a sample of unknown moisture content with a frequency band of light of a first wavelength having a first moisture absorptivity characteristic for a first time interval and providing a first signal corresponding to the magnitude of the first wavelength light reflecting from the sample. Then, the sample is irradiated with a frequency band of light of a second wavelength having a second moisture absorptivity characteristic for a second time interval and a second signal is provided which corresponds to the magnitude of the second wavelength light reflecting from the sample during the second time interval. In response to the first and second signals, a third signal is then determined which corresponds to the moisture content of the sample. It is preferable that the determining step comprises the step of correlating the first and second signals to light reflecting signals of the first and second wavelengths measured on samples of known moisture content. It may also be preferable that the correlating step comprises the step of comparing a ratio of the first and second signals to ratios of the light reflecting signals of the first and second wavelengths measured on samples of known moisture content. Further, the first and second signal providing steps may comprise the step of subtracting ambient light levels from respective measurements made during said first and second time intervals. The first wavelength may be at approximately 880 nanometers and the second may be wavelength at approximately 950 nanometers.

The invention can also be practiced by a method comprising the steps of activating a first light source of a first wavelength for a predetermined time period to direct light of the first wavelength onto a sample of a substance of unknown moisture content while measuring light adjacent to the sample to produce a first electrical signal corresponding to the magnitude of light of the first wavelength reflecting from the sample. Subsequently, a step includes activating a second light source of a second wavelength for a predetermined time period to direct light of the second wavelength onto the sample while measuring light of the second wavelength reflecting from the sample to produce a second electrical signal corresponding to the magnitude of light of the second wavelength reflecting from the sample. Then, the moisture content of the sample is determined by correlating the first and second electrical signals with data derived from measurements of light of the first and second wavelengths reflected from samples of known moisture content.

The invention may also be practiced by an apparatus comprising means for directing light of a first wavelength onto a sample of unknown moisture content during a first time period and directing light of a second wavelength onto the sample during a second time period. The apparatus further comprises means for providing first and second electrical signals respectively corresponding to light of the first and second wavelengths reflecting from the samples during the respective first and second time periods, and means responsive to the first and second electrical signals for providing a third signal corresponding to the moisture content of the sample. The first wavelength light directing means may comprise a bank of light emitting diodes emitting infrared energy having a wavelength of approximately 880 nanometers, and the second wavelength light directing means may comprise a bank of light emitting diodes emitting infrared energy having a wavelength of approximately 950 nanometers.

With such arrangement, measurements of reflected light at two discrete wavelengths having two water absorption characteristics are provided without the use of moving parts such as a prior art chopper wheel with narrow bandpass filters. In particular, rather than directing broadband light onto the sample and then filtering the spectrum to determine the spectral content at two discrete wavelengths, the sample is sequentially irradiated with light limited to two discrete wavelengths. Therefore, a broadband detector can be used to measure the reflected light at both wavelengths without the need for multiple filters and associated wheel rotating apparatus. Another advantage is that the light at the wavelengths of interest is intensified thereby providing an enhanced signal-to-noise ratio which reduces or eliminates the need for associated shading apparatus around the sensor.

BRIEF DESCRIPTION OF THE DRAWINGS

The foregoing objects and advantages will be more fully understood with reference to the drawings wherein:

FIGS. 6A-C show respective timing diagrams of the 880 and 950 nanometer wavelength drivers and the corresponding output of the IR detector.

DESCRIPTION OF THE PREFERRED EMBODIMENTS

Figure 1:
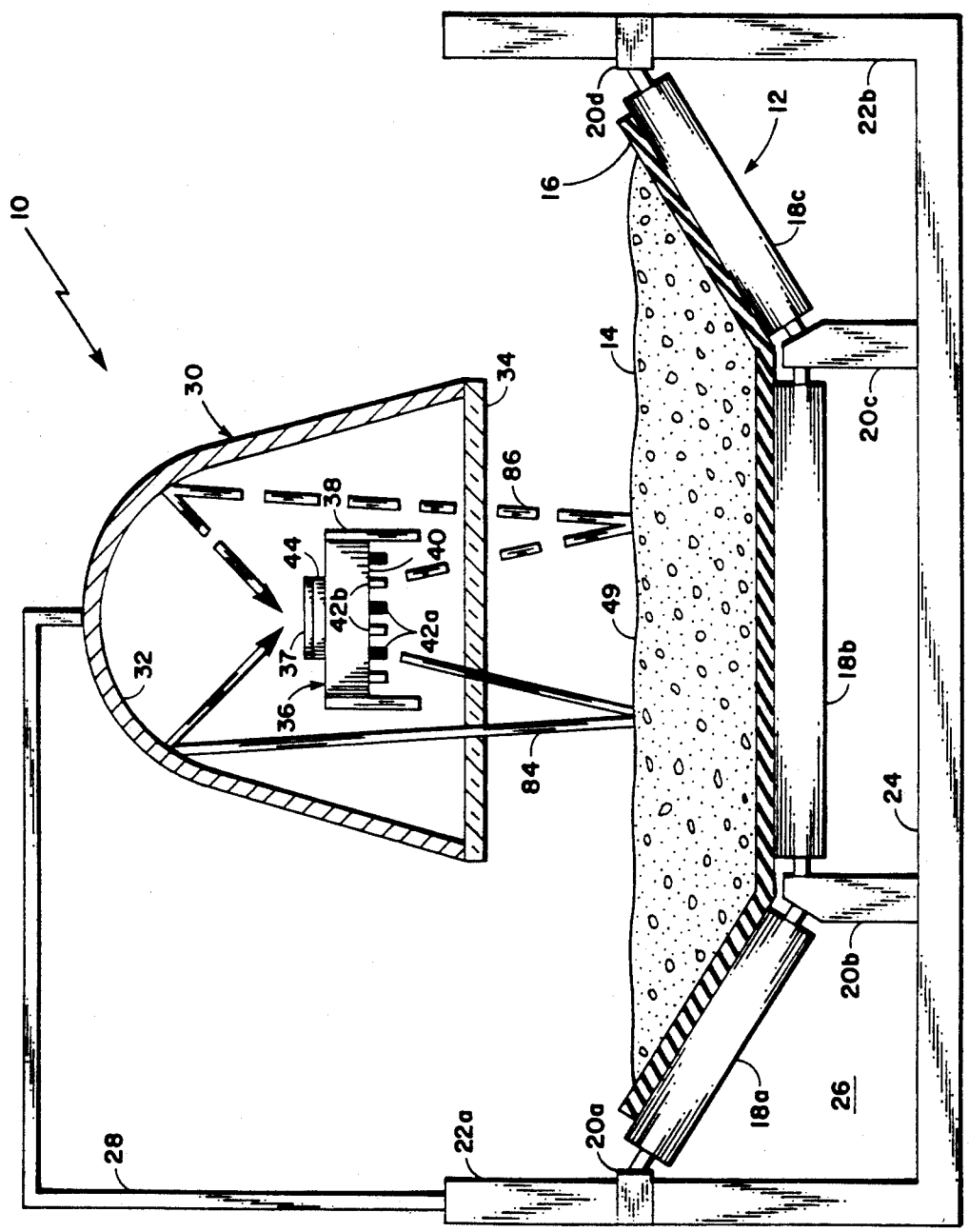
FIG. 1 is a sectioned view of a dual wavelength moisture sensor disposed above a material being transported on a conveyor belt.

Referring to FIG. 1, a dual wavelength infrared moisture sensor 10 is positioned above a conveyor 12 which carries a material or substance 14 of unknown moisture content. For purposes here, moisture content is generally defined as the weight of the water in the material divided by the material weight plus the weight of the water. This moisture content value is an important parameter in the controlling of many industrial processes such as, for example, the making of asphalt. For example, substance 14 may be sand and/or gravel which are collectively referred to as aggregate in the process of making asphalt for road paving. Conveyor 12 includes a belt 16 supported by rollers 18 $a$-$c$ which are captured by respective brackets 20$a$-$d$ mounted to the walls 22$a$ and $b$ and floor 24 of channel 26. In the depiction of FIG. 1, the substance 14 or aggregate is being conveyed towards the viewer. Infrared moisture sensor 10 is supported by a stand 28 connected to wall 22a. It may also be desirable to mount a levelling blade (not shown) between walls 22a and b to make the upper surface of aggregate 14 more uniformly level to increase the accuracy of the moisture content measuring method to be described subsequently herein.

Infrared or IR moisture sensor 10 includes a downwardly directed parabolic reflector 30 having a highly reflective or mirror-like internal surface 32. The lower open end of parabolic reflector 30 is covered by an infrared transmissive or transparent window 34 which prevents foreign matter from entering reflector 30. Typically, window 34 may be made from a clear material such as acrylic.

A dual wavelength infrared emitter section 36 is here suitably disposed within parabolic reflector 30, and includes a vertical cylinder 38 surrounding a horizontal plate, here a printed circuit board 40 on which a plurality of narrow-band light emissive devices such as photoemissive diodes or LEDs 42a and b are mounted.

Figure 2:
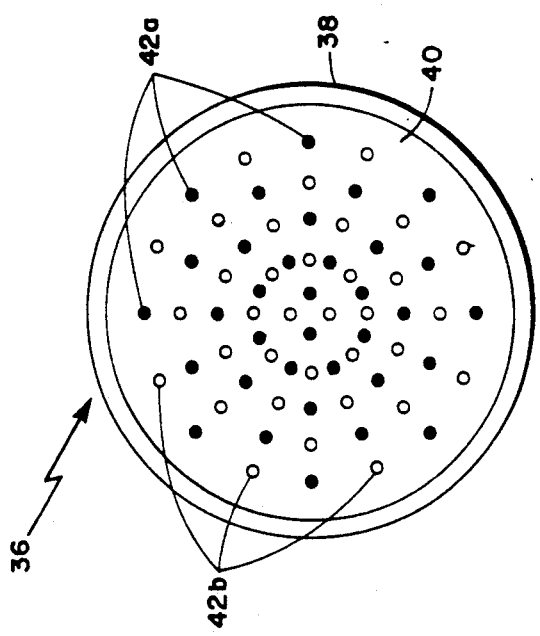
FIG. 2 is a bottom view of the moisture sensor of FIG. 1.

As shown in FIG. 2, LEDs 42a and b are spaced around printed circuit board 40 in some predetermined pattern providing a desired uniformity of emitted light here infrared energy from vertical cylinder 38. A plurality or bank of LEDs 42a are here depicted as darkened circles, and may typically represent eighteen 23-milliwatt LEDs that emit a discrete or narrow band of light or infrared energy having a center or characteristic wavelength of 880 nanometers. A plurality or bank of LEDs 42b are here depicted as open circles, and may typically represent eighteen 14-milliwatt LEDs that emit a discrete or narrow band of light or infrared energy having a center or characteristic wavelength of 950 nanometers. Infrared detector or photosensor such as photosensitive diode 44 is mounted on top of dual wavelength infrared emitter section 36 and is covered with a long pass filter 37 to filter out light below a predetermined wavelength such as, for example, 830 nanometers. One example of photosensitive diode 44 is a VTS 7080 photodiode by E. G. & G Vactec of St. Louis, Missouri. The internal surface 32 of parabolic reflector 30 is configured to direct a substantial portion of light or infrared energy entering parabolic reflector 30 onto photosensitive diode 44.

Figure 3:
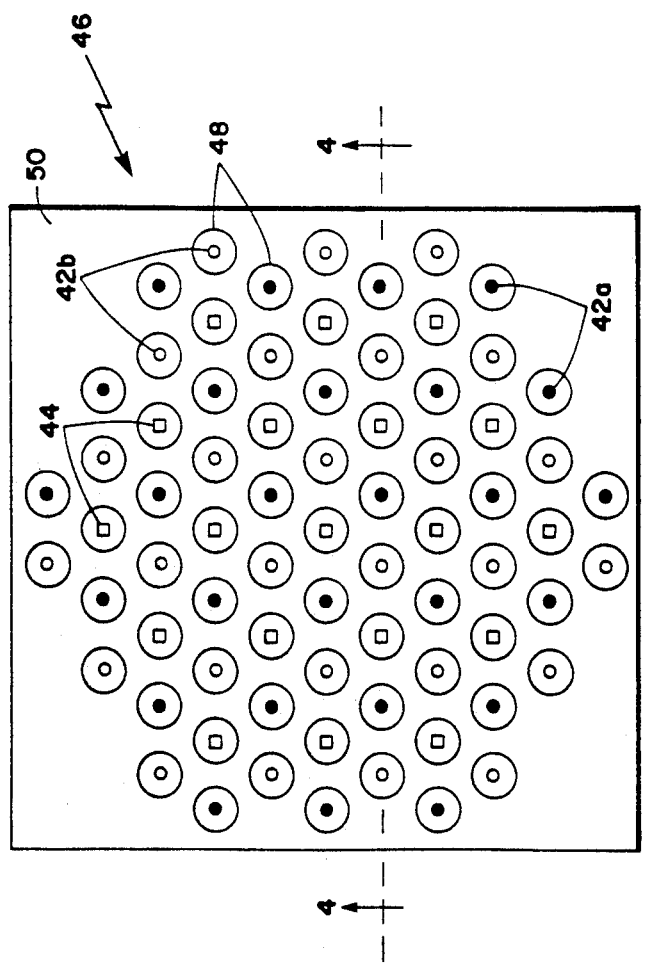
FIG. 3 is a bottom view of an alternate embodiment of a moisture sensor.
Figure 4:
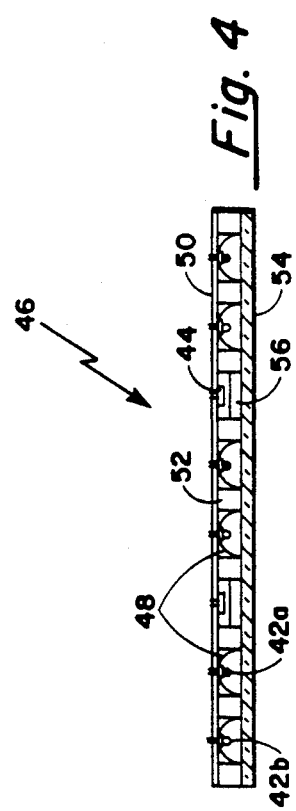
FIG. 4 is a side sectioned view of FIG. 3 taken along line 4—4.

Referring to FIGS. 3 & 4, infrared moisture sensor 46 is an alternate embodiment to infrared moisture sensor 10. Here, rather than having a large parabolic reflector 30 for the photosensitive diode 44 as in the parabolic optics configuration of FIG. 1, each infrared emitter or LED 42a and b is provided with a individual parabolic mirror 48 to direct or intensify the emitted light or infrared energy down towards the substance or aggregate 14 under test. In contrast, the vertical cylinder 38 of infrared moisture sensor 10 in FIG. 1 helps to concentrate the collectively emitted light to a relatively small region or sample portion 49 of the substance 14. In a typical array optics configuration as shown in FIGS. 3 and 4, twenty-six 23-milliwatt LEDs of 880 nanometer wavelength and twenty-six 14-milliwatt LEDs of 950 nanometers wavelength are mounted to printed circuit board 50. As shown in FIG. 3, the 880 nanometer wavelength LEDs 42a are represented by dark circles while the 950 nanometer wavelength LEDs 42b are represented by open circles. Also dispersed in the array of LEDs 42a and b are a plurality of broadband infrared detectors here photosensitive diodes 44. The LEDs 42a and b and photosensitive diodes 44 are separated by Lexan spacers 52 and the underside of infrared moisture sensor 46 is covered by an infrared transmissive shield, here an acrylic window 54 to keep foreign matter off of infrared moisture sensor 46. Each of the photosensitive diodes 44 is covered by an 830 nanometer long pass filter 56 to filter out interfering light.

Figure 5:
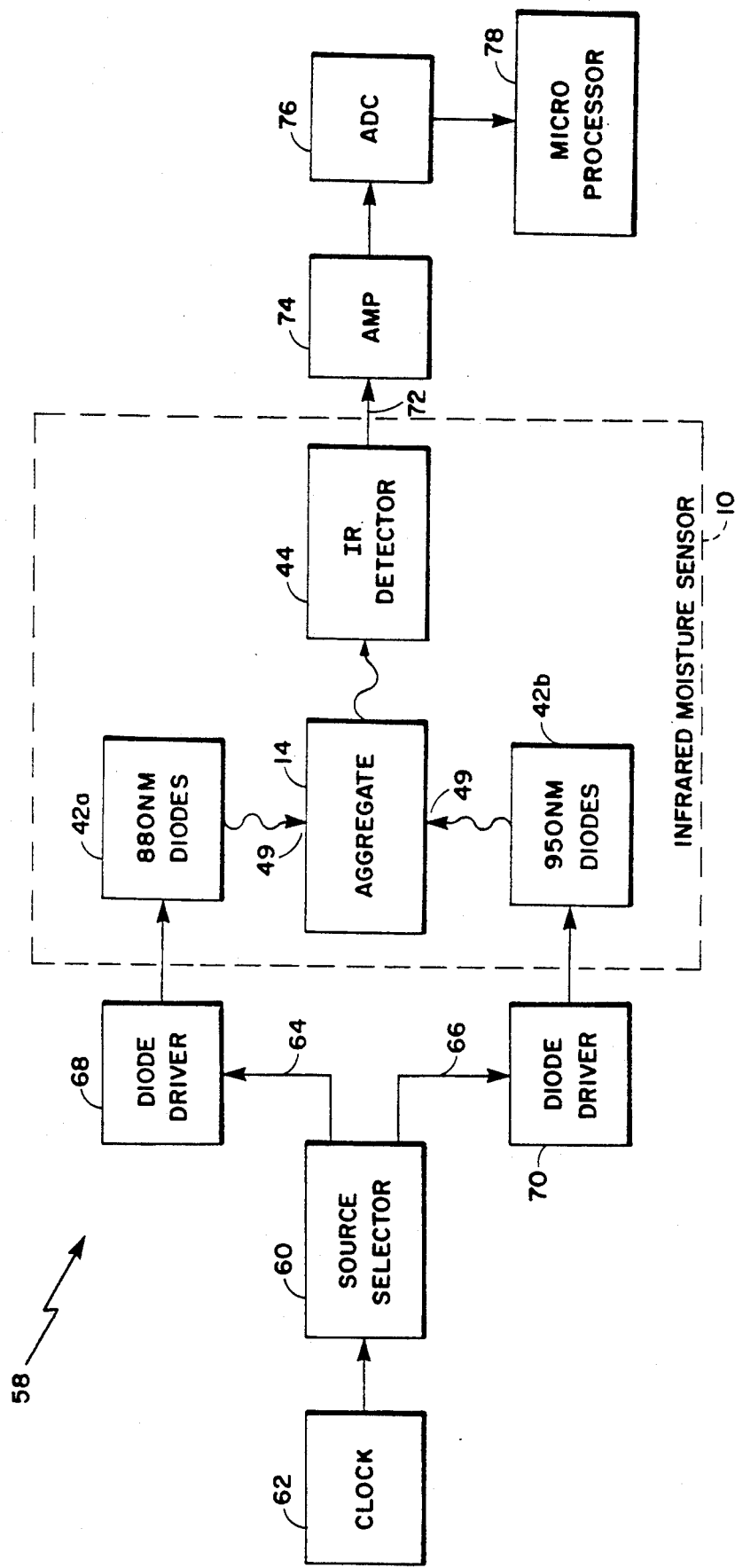
FIG. 5 is a block diagram of a moisture sensing system embodying the moisture sensor of FIGS. 1 or 3.

Referring to FIG. 5, a block diagram shows a dual wavelength moisture sensing system 58 which uses the infrared moisture sensor 10 or 46 to advantage. Source selector 60 is fed by clock 62, and provides enabling signals on lines 64 and 66 to respective diode drivers 68 and 70. In response to the enabling signals, diode drivers 68 and 70 alternately provide pulsed drive signals to respective 880 nanometer diodes 42a and 950 nanometer diodes 42b. As a result, whether using the infrared moisture sensor 10 of FIG. 1 or the alternate infrared moisture sensor 46 of FIG. 3, a sample portion 49 of the substance 14 or material here shown as aggregate is illuminated with sequential infrared light pulses or flashes of different wavelength (e.g. 880 nanometers and 950 nanometers). A portion of light reflected from aggregate 14 is incident on the IR detector 44 or photosensitive diode and, in the case of FIG. 3, a plurality or bank of photosensitive diodes 44. In response to the incident light or infrared energy, the infrared detector 44 provides a low level signal on line 72 which is amplified by amplifier 74 before being digitized by analog-to-digital converter ADC 76. The output of ADC 76 is processed by microprocessor 78 in a manner to be described subsequently.

More particularly, with reference to FIGS. 6A and B, source selector 60 receives clocking pulses such as, for example, at a 10 kilohertz rate, and initially provides an enabling signal on line 64 that causes diode driver 68 to synchronously provide a drive pulse 80 to all of the 880 nanometer wavelength diodes 42a. For example, as shown in FIG. 6A, the 880 nanometer driver 68 may typically provide a drive pulse having a time duration of 12 milliseconds during which time all of the 880 nanometer wavelength LEDs 42a are activated. In the case of the parabolic reflector optics configuration shown in FIG. 1, each of the 880 nanometer wavelength LEDs 42a turn on for 12 milliseconds and provide a directive beam of light or infrared energy down vertical cylinder 38 onto a sample portion 49 of substance 14 here shown as aggregate. In the case of the array optics configuration shown in FIG. 3, each one of the 880 nanometer wavelength LEDs 42a is turned on or activated for 12 milliseconds and each directs each own individual beam onto a sample portion 49 of substance 14. Following 12-millisecond millisecond pulse 80, the output of source selector 60 becomes inactive for 12 milliseconds, as shown in FIGS. 6A and 6B. Then an enabling pulse is provided to diode driver 70 which in turn synchronously provides a drive pulse 82 to all of the 950 nanometer wavelength diodes 42b. In a manner described above for the 880 nanometer wavelength LEDs 42a, a sample portion 49 of the substance 14 is illuminated by one or more directive beams of 950 nanometer wavelength energy. Following the termination of pulse 82, the source selector 60 outputs to diode drivers 68 and 70 are inactive for 14 milliseconds, and then the same timing sequence is initiated again. In short, all of the 880 nanometer wavelength LEDs 40a are pulsed on in unison every 50 milliseconds for a time duration or interval of 12 milliseconds, and all of the 950 nanometer wavelength LEDs 42b are pulsed on in unison every 50 milliseconds for a time duration or interval of 12 milliseconds, and the pulses are noncoincidental.

In further discussion of the operation of dual wavelength moisture sensing system 58, narrow band infrared energy from the respective 880 nanometer and 950 nanometer wavelength pulses is reflected from the sample region 49 of substance 14 as depicted in FIG. 1. More specifically, the 880 nanometer wavelength light 84 is depicted by a solid arrow, and the 950 nanometer wavelength light 86 is depicted by a dashed arrow. A portion of this light 84 and 86 enters parabolic reflector 30 and is directed onto IR detector here photosensitive diode 44. In the case of the array optics configuration of FIG. 3, individual directive beams from the LEDs 42a and b are reflected backup through window 54 and long pass filter 56 to photosensitive diodes 44 whose outputs are summed.

As shown in FIG. 6C, the IR detector output or the output of one or ganged photosensitive diodes 44 is a series or sequence of spaced pulses 88–91, each corresponding to a respective one of the pulses of light or infrared energy, emitted by respective LEDs 42a and b. For example, pulse 88 corresponds to the first 12 millisecond activation of the 880 nanometer wavelength LEDs 42a, and pulse 89 corresponds to the first 12 millisecond activation of the 950 nanometer wavelength LEDs 42b. Pulses 90 and 91 correspond to subsequent activations of respective banks of LEDs 42a and b. After amplification in amplifier 74, pulses 88–91 are converted to digital signals and the respective 12 millisecond time periods are each sampled 128 times. These samples are added and then divided by 128 to provide an average amplitude during the pulse period. It is further noted that there are inactive time periods 92 and 93 of 12 and 14 milliseconds between respective alternating wavelength light pulses 88–90. During these inactive periods 92 and 93 when neither LEDs 42a nor 42b are active, the low level electrical signal at the output of the IR detector or photosensitive diode 44 corresponds to the ambient light level. Therefore, 128 samples are also taken and averaged during time periods 92 and 93, and these values are subtracted from the respective average values for respective preceding pulses 88 and 89. Thus, the normalized average magnitudes of pulses 88 and 89, here defined as $V_1$ and $V_2$, correspond to or are representative of the magnitude of light or IR energy of respective wavelengths 880 nanometers and 950 nanometers that reflects from the sample portion 49 of the material or substance 14 being analyzed.

As is well known, light or infrared energy is absorbed by water at very specific wavelengths. In particular, infrared energy at a wavelength of 950 nanometers is more readily absorbed than infrared energy at a wavelength of 880 nanometers. Therefore, by using the reflected 880 nanometer light as a reference value corresponding to the relative characteristics or parameters of the surface of the sample portion 49, here aggregate, the reflected 950 nanometer wavelength light provides a measure or is proportional to the water moisture on the surface of the sample portion 49. More specifically, the ratio, and in particular the ratio of $(V_1-V_2)/V_1$, where $V_1$ is the larger of the two reflected voltages, provides a value representative of or corresponding to the moisture content of the sample portion 49.

In order to determine the actual moisture content of the sample, or more particularly the sampled portion 49 of material or substance 14 illuminated by LEDs 42a and b, microprocessor 78 looks up the ratio $(V_1-V_2)/V_1$ in a table of data correlating similar precalibrated ratios to moisture content. Alternatively, microprocessor 78 may calculate or interpolate the present moisture content from on site measurements on samples of known moisture content. For example, infrared moisture sensor 10 or 46 can be used to generate $(V_1-V_2)/V_1$ ratios for samples of known moisture content, and the present $(V_1-V_2)/V_1$ ratio can be interpolated therefrom. For example, a $(V_1-V_2)/V_1$ ratio can be measured for a sample that is then weighed, dried, and reweighed to determine the precise moisture content using a conventional moisture evaporation technique. This corresponding data is then entered into microprocessor 78. Next, the $(V_1-V_2)/V_1$ ratio is measured for a wetter sample and the same weighing process performed to provide another data point of $(V_1-V_2)/V_1$ to present moisture content. By interpolating these two precalibrated data points of known moisture content, the corresponding moisture content for the presently measured $(V_1-V_2)/V_1$ ratio can be calculated using well known methodology.

In summary, a first bank of LEDs 42a is activated during a first time period to illuminate a sample portion 49 with a narrow frequency band of light having a first moisture absorption characteristic. The reflected light of this wavelength $\lambda 1$ is measured during the first time period. Then, a second bank of LEDs 42b is activated during a second time period to illuminate the sample portion 49 with a narrow frequency band of light having a second moisture absorption characteristic. The reflected light of this wavelength $\lambda 2$ is measured during the second time period. Optionally, the ambient light level can be subtracted from each of the measured reflected light levels to eliminate this factor as a variable. In any event, a ratio of the reflected light levels at the two different wavelengths $\lambda 1$ and $\lambda 2$ is correlated with similar ratios derived from similarly measured samples of known moisture content. By illuminating with narrow frequency band light from two different sources such as LEDs 42a and b rather that illuminating with a broadband source and then filtering, no moving parts such as a chopper wheel with filters are required. Further a better signal-to-noise ratio is provided because of the high intensity of the light at the wavelengths of interest.

This concludes the description of the preferred embodiment. A reading of it by one skilled in the art will bring to mind many alterations and modifications without departing from the spirit and scope of the invention. Therefore, it is intended that the scope of the invention be limited only by the appended claims.

What is claimed is:

1. A method comprising the steps of:
   irradiating a sample of unknown moisture content with a first band of light from a first bank of light emitting diodes mounted on the underside of a horizontal plate, said first band of light including a first wavelength having a first moisture absorptivity characteristic and being irradiated for a first time interval;
   providing a first signal from a detector mounted above said horizontal plate, said first signal corresponding to the magnitude of said first wavelength light reflecting from said sample during said first time interval;
   irradiating said sample with a second band of light from a second bank of light emitting diodes mounted to said underside of said horizontal plate, said second bank of light including a second wavelength having a second moisture absorptivity characteristic and being irradiated for a second time interval;

providing a second signal from said detector, said second signal corresponding to the magnitude of said second wavelength light reflecting from said sample during said second time interval; and determining a third signal corresponding to the moisture content of said sample in response to said first and second signals.

2. The method recited in claim 1 wherein said determining step comprises the step of correlating said first and second signals to light reflecting signals of said first and second wavelength measured on samples of known moisture content.

3. The method recited in claim 2 wherein said correlating step comprises the step of comparing a ratio of said first and second signals to ratios of said light reflecting signals of said first and second wavelengths measured on samples of known moisture content.

4. The method recited in claim 1 wherein said first and second signal providing steps comprise the step of subtracting ambient light levels from respective measurements made during said first and second time intervals.

5. The method recited in claim 1 wherein said light of said first and second wavelengths is infrared energy.

6. The method recited in claim 1 wherein said first wavelength is approximately 880 nanometers.

7. The method recited in claim 1 wherein said second wavelength is approximately 950 nanometers.

8. The method recited in claim 1 further comprising the step of reflecting said first and second bands of light from said sample downwardly off a reflector to said detector.

9. The method recited in claim 8 wherein said reflector comprises a downwardly facing parabolic reflector.

10. The method recited in claim 1 wherein said first and second banks of light emitting diodes are surrounded by a vertically oriented cylinder for directing said first and second bands of light downwardly towards said sample.

11. The method recited in claim 1 wherein said detector is mounted to the top side of said horizontal plate.

12. The method recited in claim 11 wherein said horizontal plate is a printed circuit board.

13. The method recited in claim 1 wherein said determining step comprises the steps of taking a ratio of said first and second signals and correlating said ratio with precalibration ratios of samples of known moisture content.

14. A method of determining moisture content of a sample, comprising the steps of:

directing a first band of electromagnetic energy from a first bank of light emitting diodes each being connected to the underside of a horizontal plate and being surrounded by a downwardly facing reflector, said first band of energy having a first water absorptivity characteristic;

generating a first electrical signal from a detector mounted to said underside of said horizontal plate, said first electrical signal being representative of the magnitude of said electromagnetic energy of said first water absorptivity characteristic reflecting from said sample during a first time period;

directing a second band of electromagnetic energy onto said sample for a second time period noncoincident with said first time period, said second band of electromagnetic energy being generated from a second bank of light emitting diodes each being connected to said horizontal plate and being surrounded by a downwardly facing reflector, said second band of energy having a second water absorptivity characteristic different than said first water absorptivity characteristic;

generating a second electrical signal representative of the magnitude of said electromagnetic energy of said second water absorptivity characteristic reflecting from said sample during said second time period; and providing a value corresponding to the moisture content of said sample in response to said first and second electrical signals.

15. The method recited in claim 14 wherein said providing step comprises the step of correlating said first and second electrical signals with previously measured first and second electrical signals measured on samples of known moisture content.

16. Apparatus comprising: means comprising a first bank of light emitting diodes connected to the underside of a horizontal plate for directing light of a first wavelength onto a sample of unknown moisture content during a first time period;

means comprising a second bank of light emitting diodes connected the said underside of said horizontal plate for directing light of a second wavelength onto said sample during a second time period;

means comprising a detector for providing first and second electrical signals respectively corresponding to light of said first and second wavelengths reflecting from said sample during respective said first and second time periods;

means for preventing said light of said first and second wavelengths from propagating directly from said respective first and second banks of light emitting diodes to said detector; and means responsive to said first and second electrical signals for providing a third signal corresponding to the moisture content of said sample.

17. The apparatus recited in claim 16 wherein said light emitting diodes of said second bank emit infrared energy having a wavelength of approximately 880 nanometers.

18. The apparatus recited in claim 16 wherein said light emitting diodes of said second bank emit infrared energy having a wavelength of approximately 950 nanometers.

* * * * *